(12) United States Patent
Nishihara

(10) Patent No.: US 11,119,307 B2
(45) Date of Patent: Sep. 14, 2021

(54) OPTICAL UNIT AND ENDOSCOPE

(71) Applicant: OLYMPUS CORPORATION, Tokyo (JP)

(72) Inventor: Teruyuki Nishihara, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/934,330

(22) Filed: Jul. 21, 2020

(65) Prior Publication Data

US 2020/0348506 A1 Nov. 5, 2020

Related U.S. Application Data

(63) Continuation of application No. PCT/JP2018/028912, filed on Aug. 1, 2018.

(30) Foreign Application Priority Data

Jan. 25, 2018 (JP) .............................. JP2018-010371

(51) Int. Cl.
*A61B 1/00* (2006.01)
*A61B 1/04* (2006.01)
*G02B 23/24* (2006.01)

(52) U.S. Cl.
CPC ........ *G02B 23/243* (2013.01); *A61B 1/00009* (2013.01); *A61B 1/00064* (2013.01)

(58) Field of Classification Search
CPC .............. G02B 23/243; G02B 23/2453; A61B 1/00009; A61B 1/00064; A61B 1/00066
See application file for complete search history.

(56) References Cited

U.S. PATENT DOCUMENTS 6,195,212 B1 * 2/2001 Miyamoto ............... G02B 7/10
359/694
8,264,104 B2 9/2012 Schrader
(Continued)

FOREIGN PATENT DOCUMENTS

EP 1 560 053 A1 8/2005
JP 63-163311 A 7/1988
(Continued)

OTHER PUBLICATIONS

International Search Report dated Oct. 30, 2018 received in PCT/JP2018/028912.

*Primary Examiner* — Thai Q Tran
*Assistant Examiner* — Jose M Mesa
(74) *Attorney, Agent, or Firm* — Scully, Scott, Murphy & Presser, P.C.

(57) ABSTRACT

An optical unit includes: a first actuator for driving a first movable barrel; a second actuator for driving a second movable barrel; a first contact surface for defining a first frontmost end position which the first movable barrel takes; a second contact surface for defining a rearmost end position which the first movable barrel takes; a third contact surface for defining a frontmost end position which the second movable barrel takes; a fourth contact surface for defining a rearmost end position which the second movable barrel takes; and a contact member formed on the first movable barrel, having a fifth contact surface which is brought into contact with a distal end surface of the second movable barrel, and defining a first stop position or a second stop position.

10 Claims, 11 Drawing Sheets

(56) References Cited

U.S. PATENT DOCUMENTS

| | | |
|---|---|---|
| 8,643,228 B2 | 2/2014 | Vogel |
| 8,922,067 B2 | 12/2014 | Vogel |
| 8,946,947 B2 | 2/2015 | Kelp |
| 9,722,480 B2 | 8/2017 | Kelp |
| 2005/0197533 A1* | 9/2005 | May .................. A61B 1/00071 |
| | | 600/164 |
| 2006/0109565 A1 | 5/2006 | Watanabe et al. |
| 2019/0043910 A1* | 2/2019 | Miyazawa ........ H01L 27/14636 |

FOREIGN PATENT DOCUMENTS

| | | |
|---|---|---|
| JP | 2004-144795 A | 5/2004 |
| JP | 2005-312091 A | 11/2005 |
| JP | 2007-147849 A | 6/2007 |
| JP | 2015-075549 A | 4/2015 |
| WO | 2004/036281 A1 | 4/2004 |

* cited by examiner

OPTICAL UNIT AND ENDOSCOPE

CROSS REFERENCE TO RELATED APPLICATION

This application is a continuation application of PCT/JP2018/028912 filed on Aug. 1, 2018 and claims benefit of Japanese Application No. 2018-010371 filed in Japan on Jan. 25, 2018, the entire contents of which are incorporated herein by this reference.

BACKGROUND OF INVENTION

1. Field of the Invention

The present invention relates to an optical unit and an endoscope where a movable barrel in which an optical system is disposed is movable back and forth by a magnetic force so as to be capable of changing an optical focus position.

2. Description of the Related Art

There has been well known an image pickup apparatus which is an optical unit and can switch a focus position by moving a movable barrel in which an optical system is disposed back and force in an optical axis direction of the optical system. Such an image pickup apparatus is mounted on, besides a camera, a communication terminal with a camera, an endoscope or the like.

For example, Japanese Patent Application Laid-Open Publication No. 2007-147849 discloses a lens driving device which performs lens driving by a magnetic action for realizing miniaturization and reduction of cost by reducing the number of parts, and an image pickup apparatus which uses the lens driving device.

SUMMARY OF THE INVENTION

According to an aspect of the present invention, there is provided an optical unit which includes: an image pickup optical system configured to form an image of an object image; a first movable barrel configured to be advanceable and retractable in a direction of a photographing optical axis of the image pickup optical system; a second movable barrel configured to be advanceable and retractable in the direction of the photographing optical axis independently from the first movable barrel; an object optical system held by the first movable barrel and/or the second movable barrel, the object optical system forming a part of the image pickup optical system; a first actuator configured to drive the first movable barrel in an advancing and retracting manner along the photographing optical axis; a second actuator configured to drive the second movable barrel in an advancing and retracting manner along the photographing optical axis; a first contact surface configured to define a first frontmost end position which the first movable barrel takes by being brought into contact with a distal end surface of the first movable barrel; a second contact surface configured to define a first rearmost end position which the first movable barrel takes by being brought into contact with a proximal end surface of the first movable barrel; a third contact surface configured to define a second frontmost end position which the second movable barrel takes by being brought into contact with a distal end surface of the second movable barrel; a fourth contact surface configured to define a second rearmost end position which the second movable barrel takes by being brought into contact with a proximal end surface of the second movable barrel; and a contact member formed on the first movable barrel, having a fifth contact surface configured to be brought into contact with the distal end surface of the second movable barrel in a state where the first movable barrel is moved to the first rearmost end position or in a state where the second movable barrel is moved to the second frontmost end position, the contact member being configured to define a first stop position which the first movable barrel takes between the first frontmost end position and the first rearmost end position or to define a second stop position which the second movable barrel takes between the second frontmost end position and the second rearmost end position.

According to another aspect of the present invention, there is provided an optical unit which includes: an image pickup optical system configured to form an image of an object image; a first movable barrel configured to be advanceable and retractable in a direction of a photographing optical axis of the image pickup optical system; a second movable barrel configured to be advanceable and retractable in the direction of the photographing optical axis independently from the first movable barrel; an object optical system held by the first movable barrel and/or the second movable barrel, the object optical system forming a part of the image pickup optical system; a first actuator configured to drive the first movable barrel in an advancing and retracting manner along the photographing optical axis; a second actuator configured to drive the second movable barrel in an advancing and retracting manner along the photographing optical axis; a first contact surface configured to define a first frontmost end position which the first movable barrel takes by being brought into contact with a distal end surface of the first movable barrel; a second contact surface configured to define a first rearmost end position which the first movable barrel takes by being brought into contact with a proximal end surface of the first movable barrel; a third contact surface configured to define a second frontmost end position which the second movable barrel takes by being brought into contact with a distal end surface of the second movable barrel; a fourth contact surface configured to define a second rearmost end position which the second movable barrel takes by being brought into contact with a proximal end surface of the second movable barrel; and a contact member formed on the second movable barrel, having a fifth contact surface configured to be brought into contact with the proximal end surface of the first movable barrel in a state where the first movable barrel is moved to the first rearmost end position or in a state where the second movable barrel is moved to the second frontmost end position, the contact member being configured to define a first stop position which the first movable barrel takes between the first frontmost end position and the first rearmost end position or to define a second stop position which the second movable barrel takes between the second frontmost end position and the second rearmost end position.

According to still another aspect of the present invention, there is provided an endoscope which includes: an insertion section configured to be inserted into a subject; and an optical unit mounted on a distal end portion of the insertion section, wherein the optical unit includes: an image pickup optical system configured to form an image of an object image; a first movable barrel configured to be advanceable and retractable in a direction of a photographing optical axis of the image pickup optical system; a second movable barrel configured to be advanceable and retractable in the direction of the photographing optical axis independently from the first movable barrel; an object optical system held by the first movable barrel and/or the second movable barrel, the object optical system forming a part of the image pickup optical system; a first actuator configured to drive the first movable barrel in an advancing and retracting manner along the photographing optical axis; a second actuator configured to drive the second movable barrel in an advancing and retracting manner along the photographing optical axis; a first contact surface configured to define a first frontmost end position which the first movable barrel takes by being brought into contact with a distal end surface of the first movable barrel; a second contact surface configured to define a first rearmost end position which the first movable barrel takes by being brought into contact with a proximal end surface of the first movable barrel; a third contact surface configured to define a second frontmost end position which the second movable barrel takes by being brought into contact with a distal end surface of the second movable barrel; a fourth contact surface configured to define a second rearmost end position which the second movable barrel takes by being brought into contact with a proximal end surface of the second movable barrel; and a contact member formed on the first movable barrel, having a fifth contact surface configured to be brought into contact with the distal end surface of the second movable barrel in a state where the first movable barrel is moved to the first rearmost end position or in a state where the second movable barrel is moved to the second frontmost end position, the contact member being configured to define a first stop position which the first movable barrel takes between the first frontmost end position and the first rearmost end position or to define a second stop position which the second movable barrel takes between the second frontmost end position and the second rearmost end position.

DETAILED DESCRIPTION OF THE PREFERRED EMBODIMENTS

In this embodiment, the description is made by taking an endoscope which includes an image pickup apparatus which is an optical unit according to the present invention as an example. In the description made hereinafter, drawings based on the embodiment are schematic views. Accordingly, it must be noted that a relationship between a thickness and a width of each portion, a ratio between thicknesses of respective portions and the like differ from the corresponding relationships of portions of an actual endoscope and an actual image pickup apparatus. There may be a case where portions of the endoscope and the image pickup apparatus are described with different size relationships or different ratios between the drawings.

In the description of a configuration made hereinafter, an endoscope having the image pickup apparatus is described by taking a so-called flexible endoscope which includes a flexible insertion section to be inserted into a digestive organ at an upper portion or a lower portion of a living body as an example. However, the present invention is not limited to such an endoscope, and the present invention provides a technique which is also applicable to a so-called rigid endoscope which is used for surgery and includes a rigid insertion section.

The image pickup apparatus is not limited to an image pickup apparatus mounted on a medical equipment such as an endoscope. Since the image pickup apparatus can be miniaturized, the image pickup apparatus can also be adopted by a mobile phone with a camera, for example.

Hereinafter, the image pickup apparatus and the endoscope according to one aspect of the present invention are described with reference to drawings.

Figure 1:
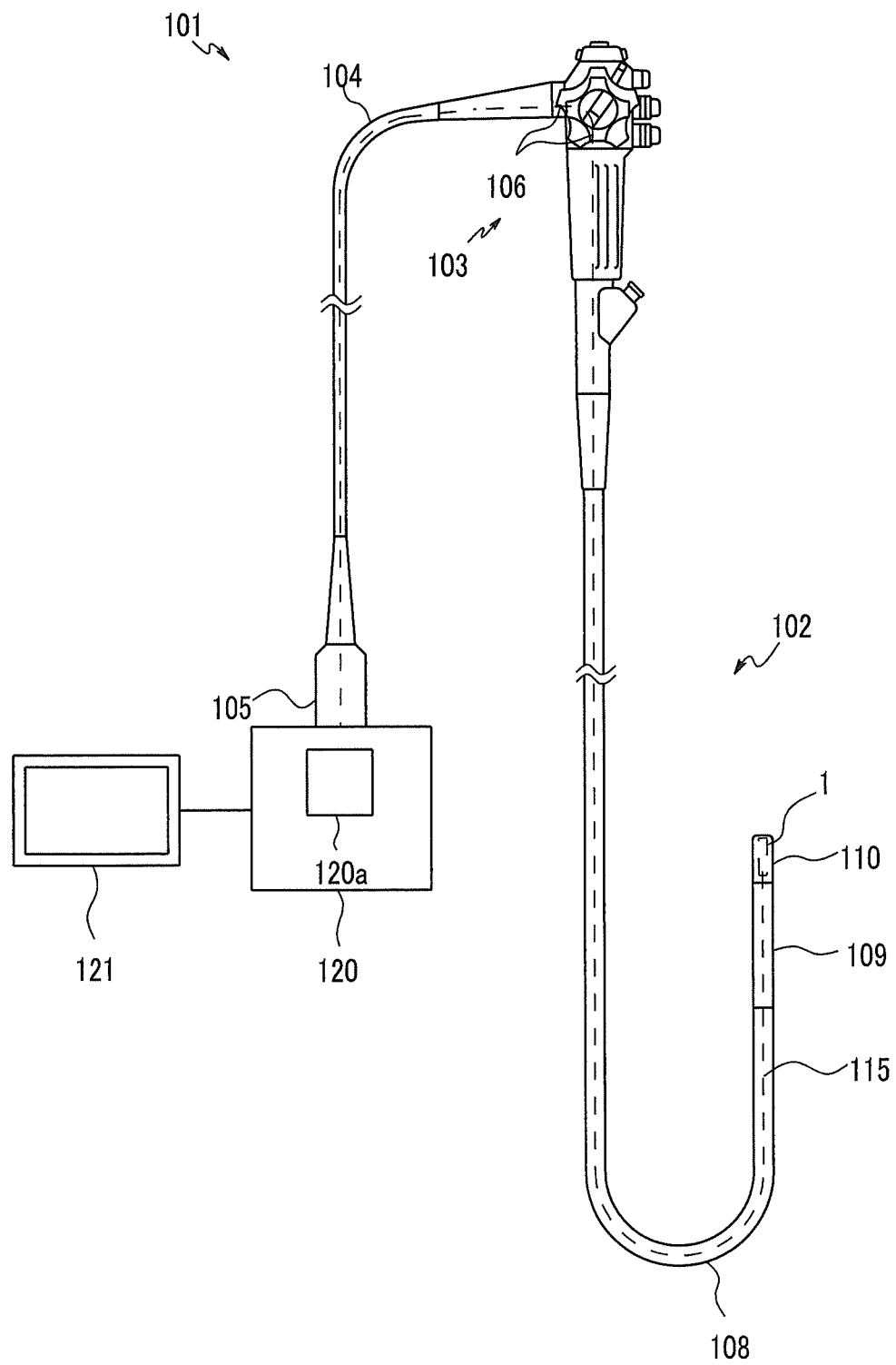
FIG. 1 is a view showing an external appearance of an endoscope which includes an image pickup apparatus which is an optical unit according to one aspect of the present invention.
Figure 2:
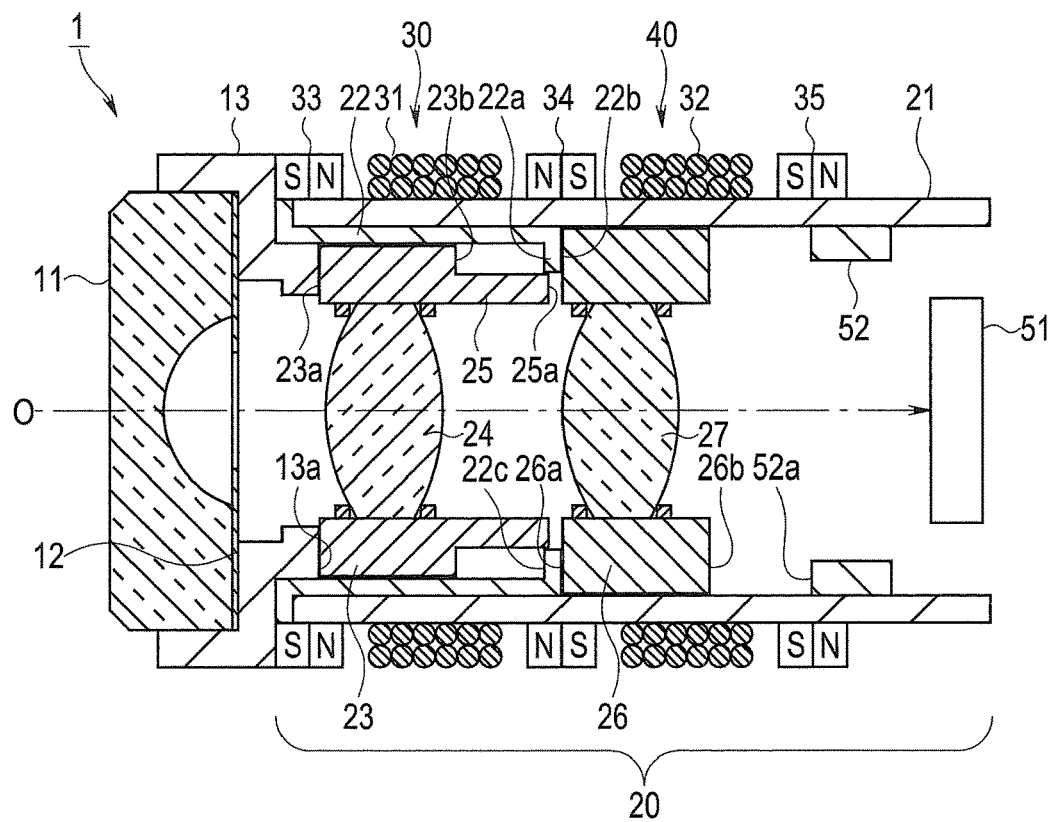
FIG. 2 is a cross-sectional view showing a configuration of the image pickup apparatus at a first focus position according to one aspect of the present invention.
Figure 3:
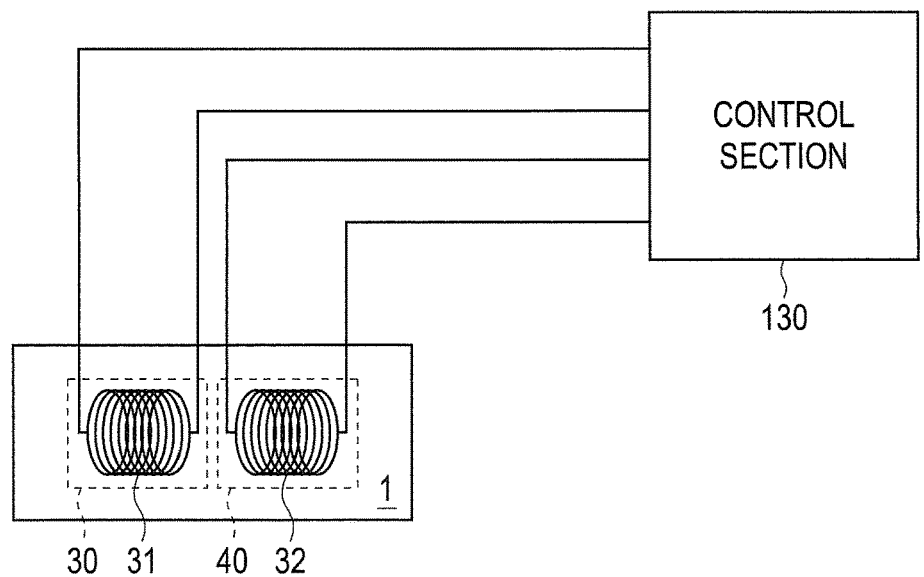
FIG. 3 is a block diagram showing a control section for supplying an electric current to coils of actuators of the image pickup unit according to one aspect of the present invention.

FIG. 1 is a view showing an external appearance of an endoscope which includes an image pickup apparatus according to one aspect of the present invention. FIG. 2 is a cross-sectional view showing a configuration of the image pickup apparatus at a first focus position. FIG. 3 is a block diagram showing a control section for supplying an electric current to coils of actuators of an image pickup unit.

Figure 4:
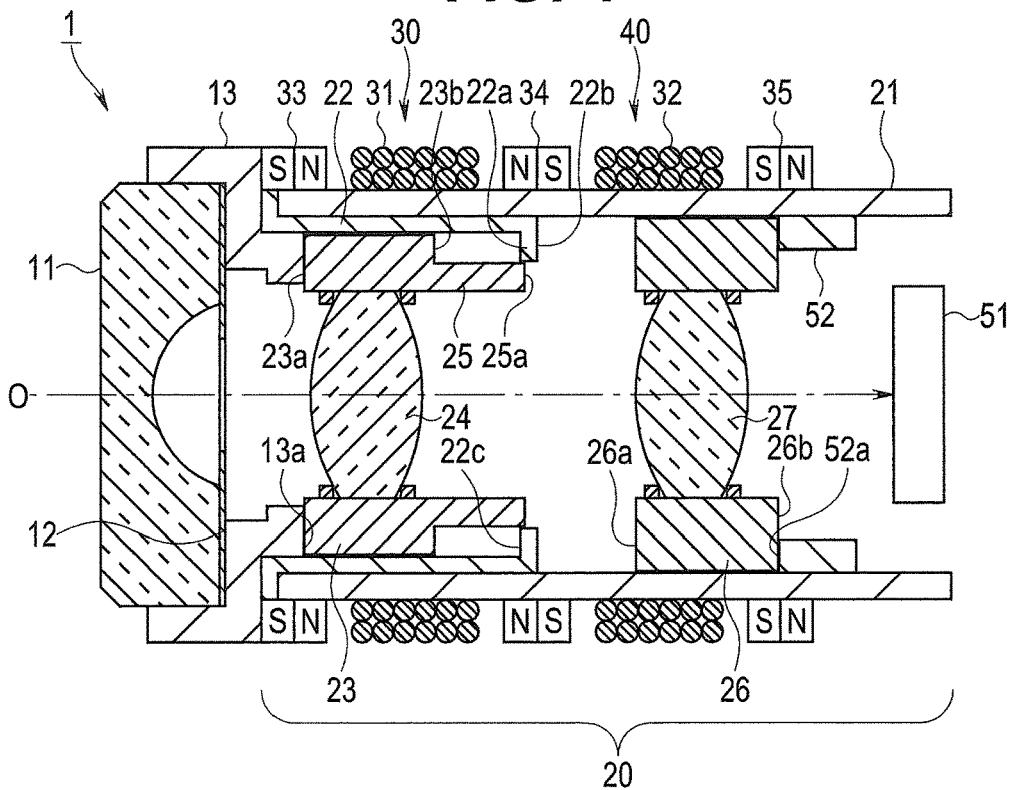
FIG. 4 is a cross-sectional view showing the configuration of the image pickup apparatus at a second focus position according to one aspect of the present invention.
Figure 5:
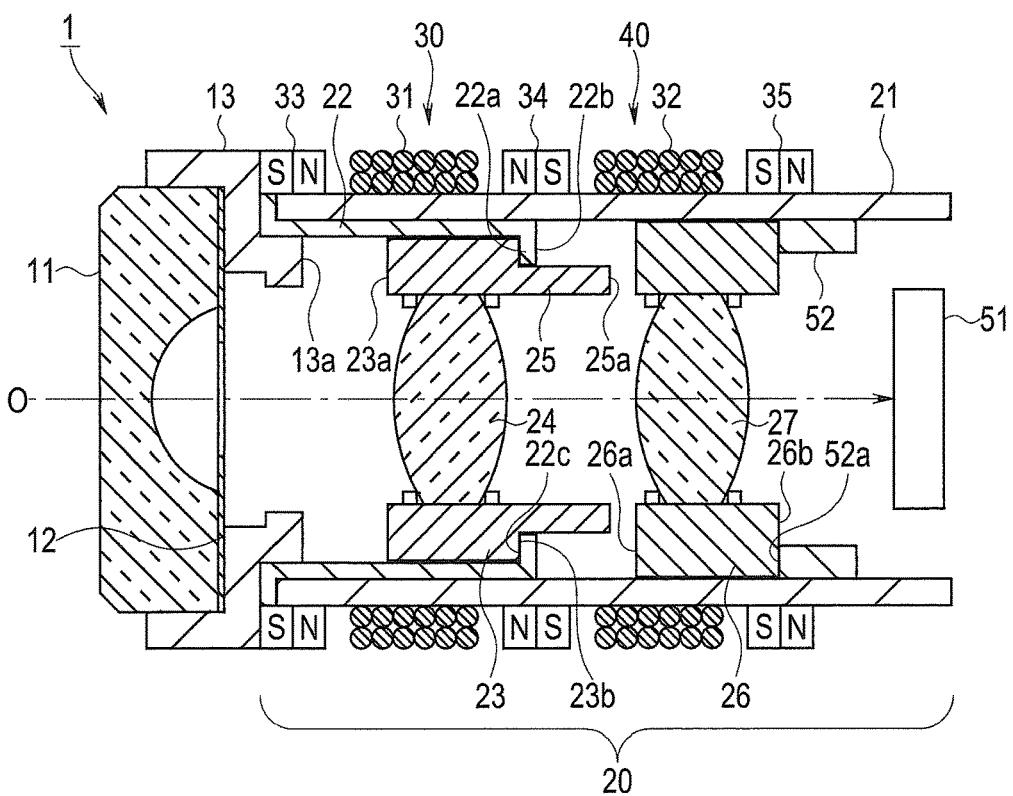
FIG. 5 is a cross-sectional view showing the configuration of the image pickup apparatus at a third focus position according to one aspect of the present invention.
Figure 6:
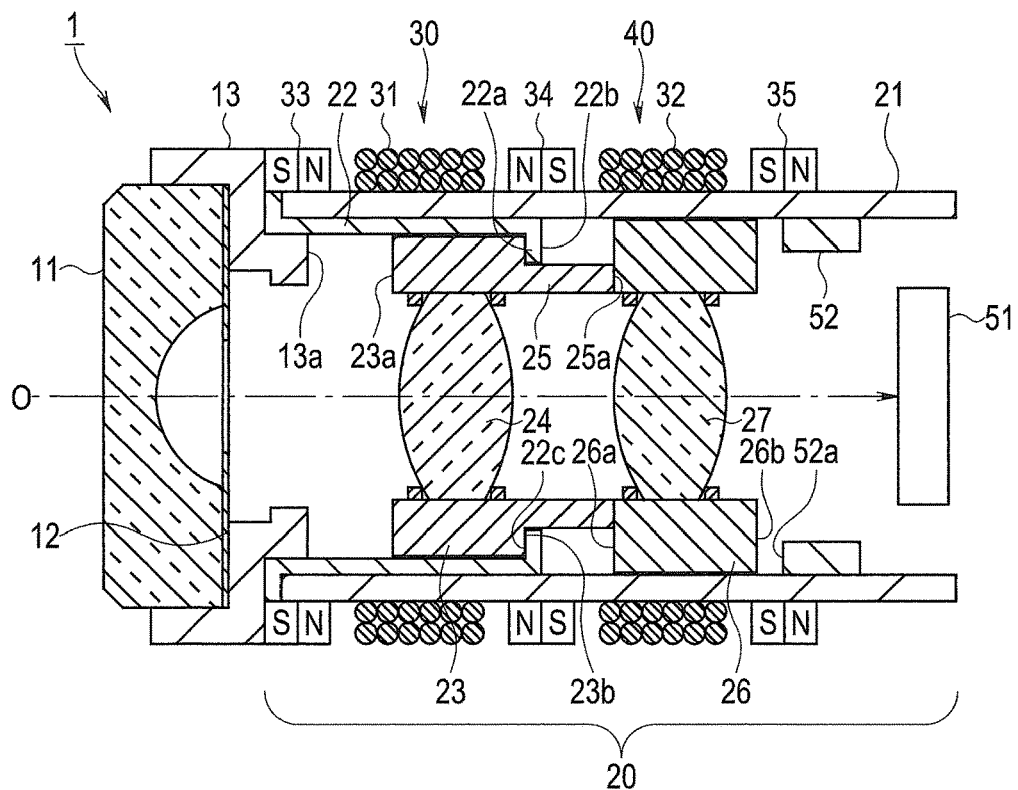
FIG. 6 is a cross-sectional view showing the configuration of the image pickup apparatus at a fourth focus position according to one aspect of the present invention.
Figure 7:
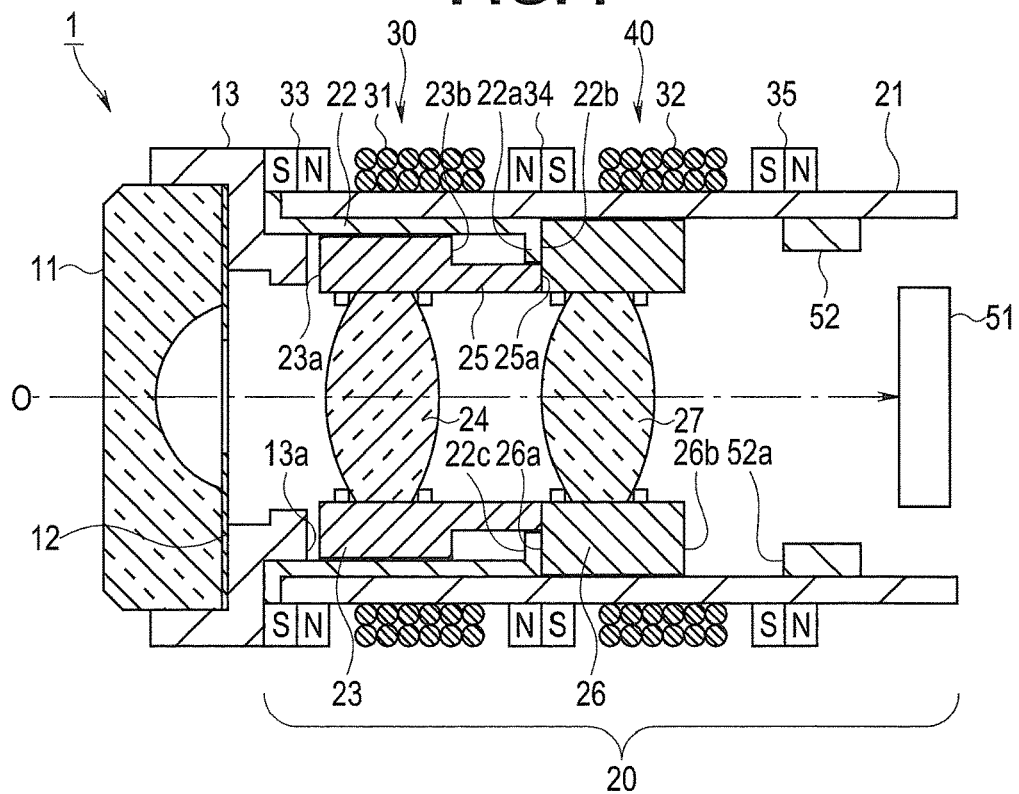
FIG. 7 is a cross-sectional view showing the configuration of the image pickup apparatus at a fifth focus position according to one aspect of the present invention.
Figure 8:
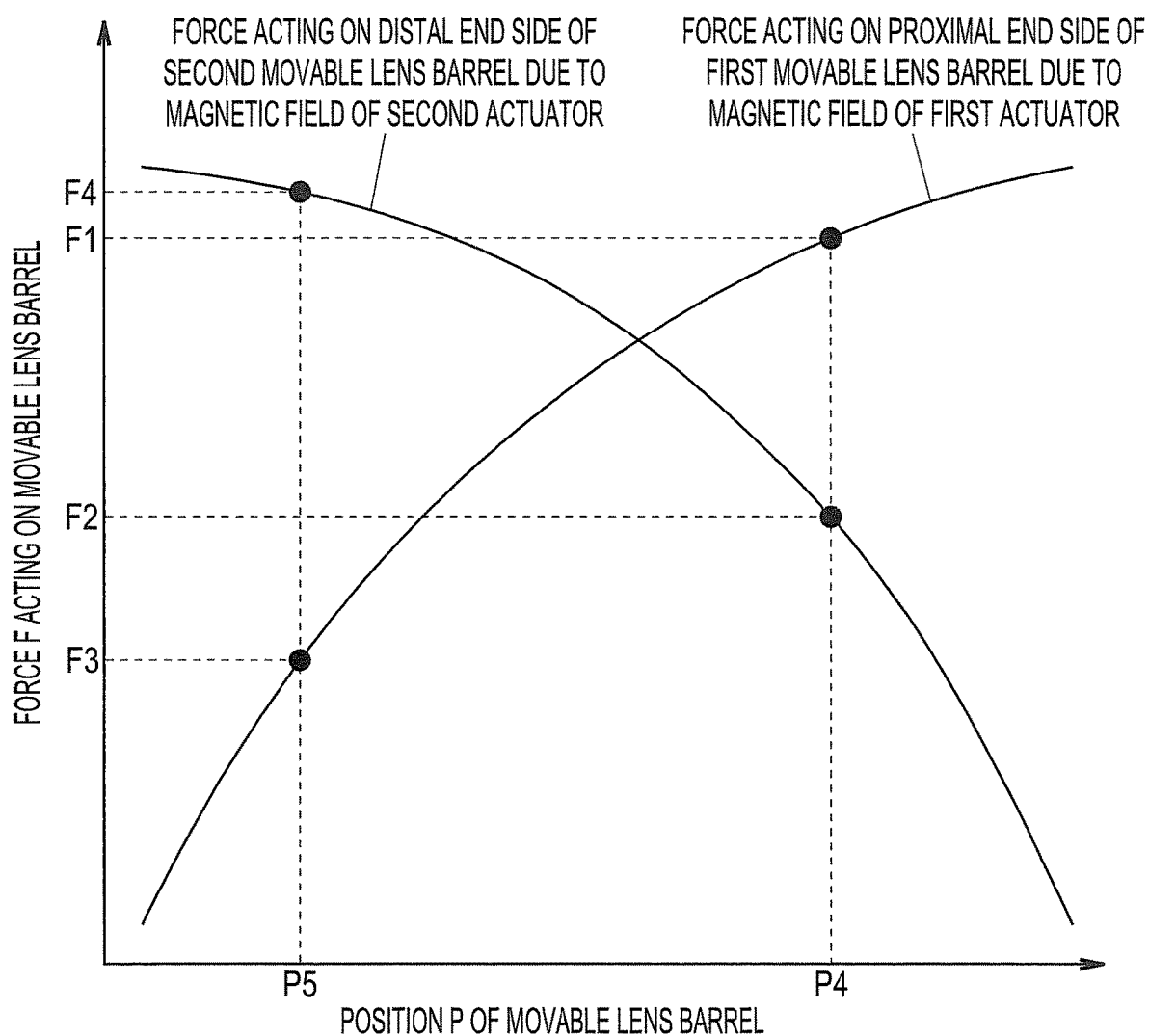
FIG. 8 is a graph showing a relationship between positions of respective movable lens barrels at the fourth focus position and the fifth focus position and forces acting due to a magnetic force according to one aspect of the present invention.
Figure 9:
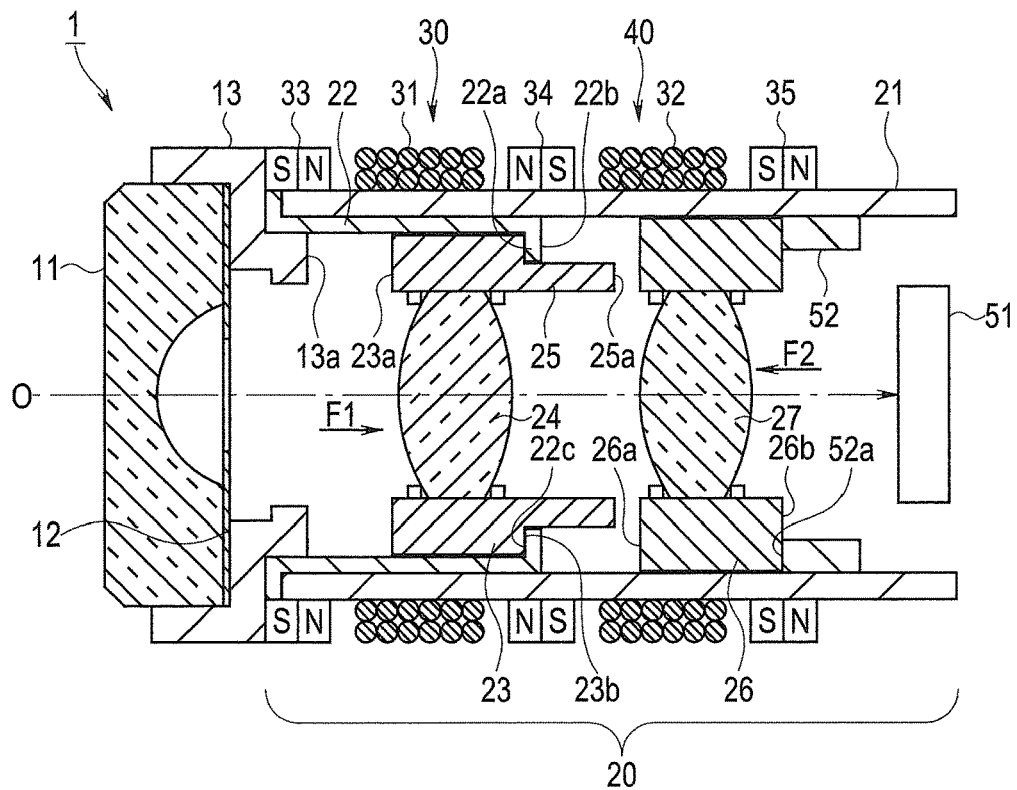
FIG. 9 is a cross-sectional view of the image pickup apparatus showing forces acting on the respective movable lens barrels at the third focus position according to one aspect of the present invention.
Figure 10:
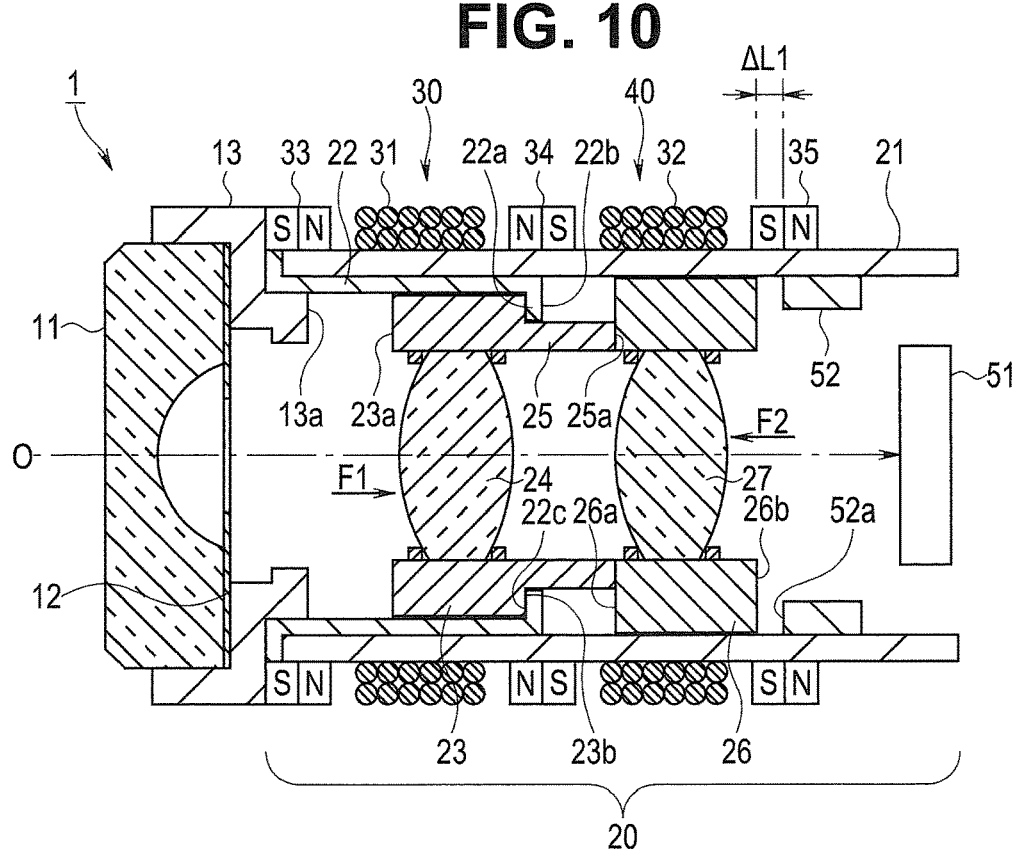
FIG. 10 is a cross-sectional view of the image pickup apparatus showing forces acting on the respective movable lens barrels at the fourth focus position according to one aspect of the present invention.
Figure 11:
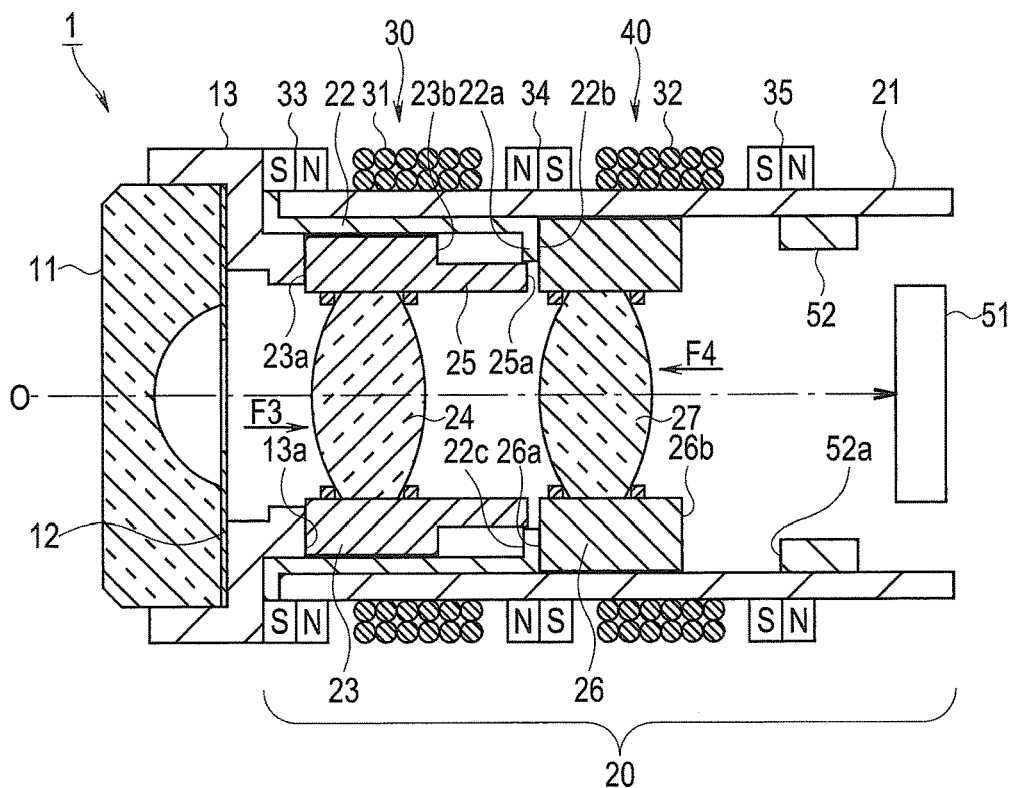
FIG. 11 is a cross-sectional view of the image pickup apparatus showing forces acting on the respective movable lens barrels at the first focus position according to one aspect of the present invention.
Figure 12:
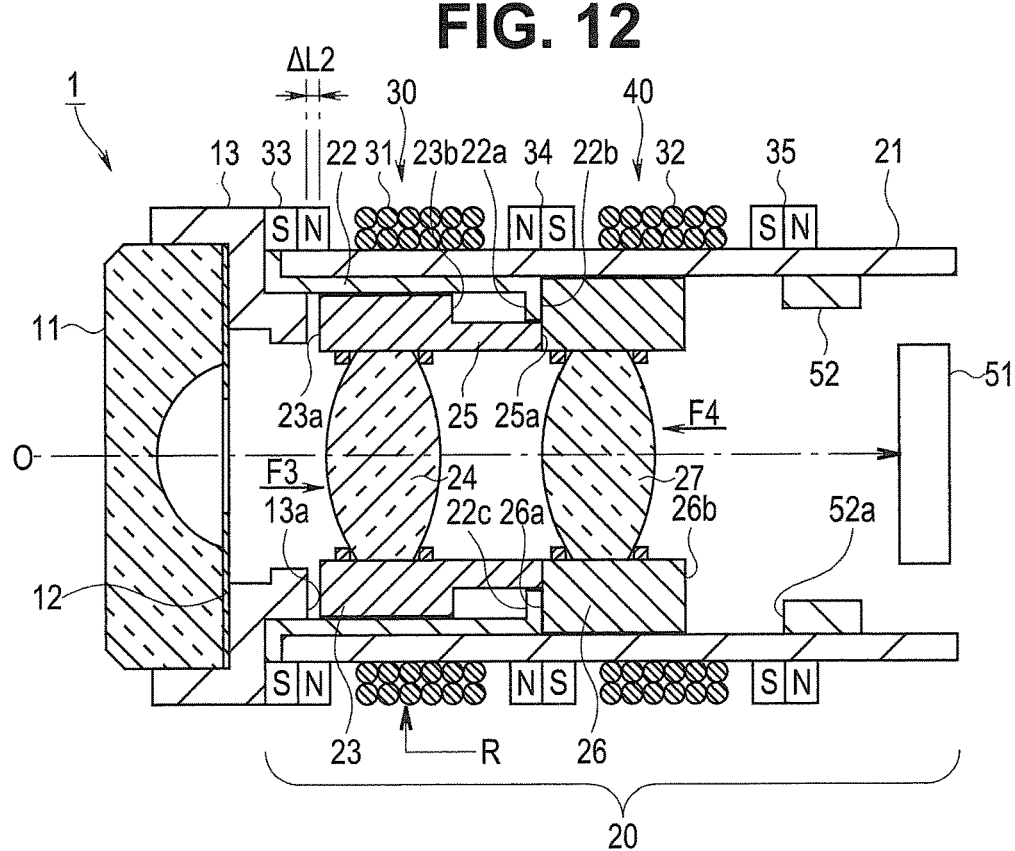
FIG. 12 is a cross-sectional view of the image pickup apparatus showing forces acting on the respective movable lens barrels at the fifth focus position according to one aspect of the present invention.

FIG. 4 is a cross-sectional view showing the configuration of the image pickup apparatus according to a second focus position. FIG. 5 is a cross-sectional view showing the configuration of the image pickup apparatus according to a third focus position. FIG. 6 is a cross-sectional view showing the configuration of the image pickup apparatus according to a fourth focus position. FIG. 7 is a cross-sectional view showing the configuration of the image pickup apparatus according to a fifth focus position. FIG. 8 is a graph showing a relationship between positions of respective movable lens barrels at the fourth focus position and the fifth focus position and forces acting due to a magnetic force. FIG. 9 is a cross-sectional view of the image pickup apparatus showing forces acting on the respective movable lens barrels at the third focus position. FIG. 10 is a cross-sectional view of the image pickup apparatus showing forces acting on the respective movable lens barrels at the fourth focus position. FIG. 11 is a cross-sectional view of the image pickup apparatus showing forces acting on the respective movable lens barrels at the first focus position. FIG. 12 is a cross-sectional view of the image pickup apparatus showing forces acting on the respective movable lens barrels at the fifth focus position.

First, one example of a configuration of the endoscope 101 having the image pickup apparatus 1 according to the present invention is described with reference to FIG. 1.

The endoscope 101 according to this embodiment is configured such that the endoscope 101 can be introduced into a subject such as a human body and optically picks up an image of a predetermined observation site in the subject.

The subject into which the endoscope 101 is introduced is not limited to a human body, and may be another living body or may be an artificial structure such as a machine or a building.

The endoscope 101 is mainly formed of: an insertion section 102 which is introduced into a subject; an operation section 103 which is positioned on a proximal end of the insertion section 102; and a universal cord 104 which extends from a side portion of the operation section 103.

The insertion section 102 is formed by connecting: a distal end portion 110 which is disposed on a distal end of the insertion section 102; a bending portion 109 which is bendable and is disposed on a proximal end side of the distal end portion 110; and a flexible tube portion 108 which has flexibility, is disposed on a proximal end side of the bending portion 109, and is connected to a distal end side of the operation section 103.

Although the description is made in detail later, the image pickup apparatus 1 is mounted on the distal end portion 110. An angle operation knob 106 for operating bending of the bending portion 109 is mounted on the operation section 103.

An endoscope connector 105 which is connected to an external device 120 is mounted on a proximal end portion of the universal cord 104. The external device 120 to which the endoscope connector 105 is connected is connected to an image display section 121 such as a monitor via a cable.

The endoscope 101 also includes: a composite cable 115 (not shown) which passes through the universal cord 104, the operation section 103, and the insertion section 102; and a bundle of optical fibers (not shown) which transmit illumination light from a light source section mounted in the external device 120.

The composite cable 115 electrically connects the endoscope connector 105 with the image pickup apparatus 1. By connecting the endoscope connector 105 to the external device 120, the image pickup apparatus 1 is electrically connected to the external device 120 via the composite cable 115.

A supply of electricity from the external device 120 to the image pickup apparatus 1 and a communication between the external device 120 and the image pickup apparatus 1 are performed via the composite cable 115.

An image processing section is disposed in the external device 120. The image processing section generates a video signal based on an image pickup device output signal outputted from the image pickup apparatus 1, and outputs the video signal to the image display section 121. In other words, in this embodiment, an optical image (endoscope image) which is picked up by the image pickup apparatus 1 is displayed on the image display section 121 as a video.

The endoscope 101 is not limited to the configuration where the endoscope 101 is connected to the external device 120 or the image display section 121. For example, the endoscope 101 may be configured such that the endoscope includes a part or the whole image processing section or monitor.

The bundle of optical fibers (not shown) are configured to transmit light emitted from the light source section of the external device 120 to an illumination window which forms an illumination light radiating section of the distal end portion 110. The light source section may be configured such that the light source section is disposed in the operation section 103 or the distal end portion 110 of the endoscope 101.

Next, the configuration of the image pickup apparatus 1 which is an optical unit according to this embodiment is described in detail hereafter.

As shown in FIG. 2, the image pickup apparatus 1 includes: a fixed lens 11 which is an object optical system forming an observation window mounted on a most distal end; and a first fixed lens barrel 13 which holds and fixes the fixed lens 11 and an aperture 12, and is a fixed barrel made of non-magnetic metal such as stainless steel, ceramic, or a rigid resin.

In the image pickup apparatus 1, a movable lens unit 20 which is configured to perform multifocus switching is disposed behind the fixed lens barrel 13 (on a proximal end side).

The image pickup apparatus 1 also includes an image pickup device 51 which is an image sensor such as a CCD or a CMOS and is fixed to an image pickup device holding frame not shown in the drawing. Note that the image pickup device holding frame which holds the image pickup device 51 is continuously disposed behind the movable lens unit 20.

The movable lens unit 20 includes: a second fixed lens barrel 21 which is a fixed barrel having an approximately sleeve shape; a stopper barrel 22 which is a fixed barrel which is fitted in a distal end of the second fixed lens barrel 21 by fitting; a first movable lens barrel 23 which is a first movable barrel for holding a first movable lens 24 which is an object optical system; and a second movable lens barrel 26 which is a second movable barrel for holding a second movable lens 27 which is an object optical system.

The second fixed lens barrel 21 and the stopper barrel 22 are made of non-magnetic metal such as stainless steel or a rigid resin. An inward flange 22a which extends inward in a radial direction is formed on a proximal end of the stopper barrel 22.

This inward flange 22a forms a movement stopper which defines movement positions of the first movable lens barrel 23 and the second movable lens barrel 26. Note that the stopper barrel 22 may be integrally formed with the second fixed lens barrel 21.

The first movable lens barrel 23 and the second movable lens barrel 26 are disposed in a row in the second fixed lens barrel 21 or the stopper barrel 22 in an advanceable and retractable manner along a photographing optical axis O. The first movable lens barrel 23 and the second movable lens barrel 26 are respectively formed of a magnetic body having an approximately barrel shape made of an iron-based alloy such as permalloy.

The movement of the first movable lens barrel 23 toward a front end side is restricted as a distal end surface 23a of the first movable lens barrel 23 is brought into contact with a proximal end surface 13a of the first fixed lens barrel 13 which forms a stopper. In other words, the proximal end surface 13a of the first fixed lens barrel 13 forms a first contact surface which defines a frontmost end movement position which the first movable lens barrel 23 takes.

A stepped portion is formed on a proximal end portion of the first movable lens barrel 23 such that an outer diameter of the stepped portion has a narrowed outer diameter thus forming a contact portion 25 having a predetermined length and a narrow diameter. An outer diameter of the contact portion 25 is set such that the contact portion 25 passes through the inward flange 22a without contacting the inward flange 22a of the stopper barrel 22.

The contact portion 25 has a predetermined length which allows the contact portion 25 to extend toward a second movable lens barrel 26 side beyond the inward flange 22a. The predetermined length of the contact portion 25 can be changed as desired.

The movement of the first movable lens barrel 23 toward the rear end side is restricted as a surface 23b on a rear side (proximal end side) of the first movable lens barrel 23 formed by forming the stepped portion on an intermediate portion of the first movable lens barrel 23 is brought into contact with an end surface 22c on a distal end side of the inward flange 22a of the stopper barrel 22. In other words, the end surface 22c on the distal end side of the inward flange 22a forms a second contact surface which defines a rearmost end movement position which the first movable lens barrel 23 takes.

The movement of the first movable lens barrel 23 in a rear end direction is also restricted as an end surface 25a of the contact portion 25 is brought into contact with a distal end surface 26a of the second movable lens barrel 26.

The movement of the second movable lens barrel 26 to the frontmost end is restricted as the distal end surface 26a is brought into contact with an end surface 22b on a proximal end side of the inward flange 22a of the stopper barrel 22. In other words, the end surface 22b on the proximal end side of the inward flange 22a forms a third contact surface which defines a frontmost end movement position which the second movable lens barrel 26 takes.

The movement of the second movable lens barrel 26 in a front end direction is also restricted as the distal end surface 26a of the second movable lens barrel 26 is brought into contact with the end surface 25a of the contact portion 25 of the first movable lens barrel 23.

A stopper 52 having a ring shape, for example, is formed on a proximal end portion of the second fixed lens barrel 21. The movement of the second movable lens barrel 26 toward a rear end side is restricted as a proximal end surface 26b of the second movable lens barrel 26 is brought into contact with a distal end surface 52a of the stopper 52. In other words, the distal end surface 52a of the stopper 52 forms a fourth contact surface which defines a rearmost end movement position which the second movable lens barrel 26 takes.

The end surface 25a of the contact portion 25 of the first movable lens barrel 23 forms a fifth contact surface which restricts advancing and retracting movement of the first movable lens barrel 23 and the second movable lens barrel 26 at positions between the frontmost end movement positions and the rearmost end movement position of the respective first movable lens barrel 23 and the second movable lens barrel 26.

Three magnets, that is, a first magnet 33, a second magnet 34, and a third magnet 35 are disposed on an outer peripheral portion of the second fixed lens barrel 21 in a spaced-apart manner with a predetermined distance. These three magnets, that is, the first magnet 33, the second magnet 34, and the third magnet 35 are formed in a ring shape, for example, and are fixed to the outer peripheral portion of the second fixed lens barrel 21 such that respective pairs of SN poles having opposite polarities opposedly face each other.

Two coils, that is, a first coil 31 and a second coil 32 are wound around the outer peripheral portion of the second fixed lens barrel 21 such that the first coil 31 is disposed between the first magnet 33 and the second magnet 34 disposed adjacently to each other and the second coil 32 is disposed between the second magnet 34 and the third magnet 35 disposed adjacently to each other.

The first coil 31, the first magnet 33, and the second magnet 34 form a first actuator 30 which functions as a two-focus switching actuator. The second coil 32, the second magnet 34, and the third magnet 35 form a second actuator 40 which functions as a two-focus switching actuator.

In this manner, in the second fixed lens barrel 21, the first actuator 30 and the second actuator 40 which drive the first movable lens barrel 23 and the second movable lens barrel 26 respectively in an advancing and retracting manner along a photographing optical axis O are disposed in a row in a front and rear direction (a direction along the photographing optical axis O).

The first actuator 30 drives the first movable lens barrel 23, and the second actuator 40 drives the second movable lens barrel 26. These two actuators, that is, the first actuator 30 and the second actuator 40 are arranged in a row in the longitudinal axis direction along the photographing optical axis O of the second fixed lens barrel 21.

Accordingly, two actuators, that is, the first actuator 30 and the second actuator 40 can use the second magnet 34 in common. With such a configuration, the first actuator 30 and the second actuator 40 which form two two-focus switching electromagnetic actuators can reduce a cost by reducing the number of magnets by one and can shorten (miniaturize) a length of the image pickup apparatus 1 in a direction along the photographing optical axis O.

As shown in FIG. 3, with respect to two actuators, that is, the first actuator 30 and the second actuator 40, with a supply of an electric current to two coils, that is, the first coil 31 and the second coil 32 from a control section 130 incorporated in the external device 120, a drive control of the first movable lens barrel 23 and the second movable lens barrel 26 is performed.

The drive control of the first movable lens barrel 23 or the second movable lens barrel 26 is performed by operating switches mounted on the operation section 103 of the endoscope 101 by a user. The control section 130 may be incorporated in the endoscope 101.

In the image pickup apparatus 1 having the above-mentioned configuration, when the first movable lens 24 and the second movable lens 27 are used as focusing lenses, by moving the first movable lens barrel 23 and the second movable lens barrel 26 respectively in an advancing and retracting manner along the photographing optical axis O by the first actuator 30 and the second actuator 40, it is possible to switch focusing positions corresponding to a plurality of distances with respect to a site to be examined.

The image pickup apparatus 1 may be configured such that both the first movable lens 24 and the second movable lens 27 are formed of a zoom lens and these lenses can perform enlarged/shrunken observation.

A plurality, five in this embodiment, of movement positions of the first movable lens barrel 23 and the second movable lens barrel 26 in the image pickup apparatus 1 are described in detail hereinafter.

First, the description is made with respect to the first observation position shown in FIG. 2 which is a first focus position where the first movable lens barrel 23 and the second movable lens barrel 26 are moved to the frontmost end positions respectively.

By supplying electricity to the first coil 31 of the first actuator 30 in a predetermined direction, the first movable lens barrel 23 is driven toward the front end side along the photographing optical axis O due to a generated magnetic field, and the distal end surface 23a is brought into contact with the proximal end surface 13a of the first fixed lens barrel 13 and is stopped.

Then, the supply of electricity to the first coil 31 is stopped. In this state, the first movable lens barrel 23 is held in a stopped state at the frontmost end position to which the first movable lens barrel 23 is attracted by a magnetic force from the first magnet 33.

By supplying electricity to the second coil 32 of the second actuator 40 in a predetermined direction, the second movable lens barrel 26 is driven toward a front end side along the photographing optical axis O due to a generated magnetic field, and the distal end surface 26a is brought into contact with the end surface 22b on the proximal end side of the inward flange 22a of the stopper barrel 22 and is stopped.

Then, the supply of electricity to the second coil 32 is stopped. In this state, the second movable lens barrel 26 is held in a stopped state at the frontmost end position to which the second movable lens barrel 26 is attracted by a magnetic force from the second magnet 34.

With such an operation, the image pickup apparatus 1 assumes the first observation position where the first movable lens barrel 23 and the second movable lens barrel 26 are moved to the frontmost end positions respectively.

Next, as shown in FIG. 4, the description is made with respect to a second observation position which is a second focus position where the first movable lens barrel 23 is moved to the frontmost end position and the second movable lens barrel 26 is moved to the rearmost end position.

The first movable lens barrel 23 is driven to the frontmost end position by the first actuator 30 in the same manner as the first observation position, and assumes a state where a stopped state to which the first movable lens barrel 23 is attracted by a magnetic force from the first magnet 33 is held.

By supplying electricity to the second coil 32 of the second actuator 40 in a direction opposite to the above-mentioned predetermined direction, the second movable lens barrel 26 is driven toward the rear end side along the photographing optical axis O due to a generated magnetic field, and the proximal end surface 26b is brought into contact with the distal end surface 52a of the stopper 52 and is stopped.

Then, the supply of electricity to the second coil 32 is stopped. In this state, the second movable lens barrel 26 is held in a stopped state at the rearmost end position to which the second movable lens barrel 26 is attracted by a magnetic force from the third magnet 35.

With such an operation, the image pickup apparatus 1 assumes a second observation position where the first movable lens barrel 23 is moved to the frontmost end position and the second movable lens barrel 26 is moved to the rearmost end positions.

Next, as shown in FIG. 5, the description is made with respect to a third observation position which is a third focus position where the first movable lens barrel 23 and the second movable lens barrel 26 are moved to the rearmost end positions respectively.

By supplying electricity to the first coil 31 of the first actuator 30 in a direction opposite to the above-mentioned predetermined direction, the first movable lens barrel 23 is driven toward a rear end side along the photographing optical axis O due to a magnetic force received from a generated magnetic field, and the surface 23b on the proximal end side formed by forming the stepped portion on the intermediate portion of the first movable lens barrel 23 is brought into contact with the end surface 22c on the distal end side of the inward flange 22a of the stopper barrel 22 and is stopped.

Then, the supply of electricity to the first coil 31 is stopped. In this state, the first movable lens barrel 23 is held in a stopped state at the rearmost end position to which the first movable lens barrel 23 is attracted by a magnetic force from the second magnet 34.

The second movable lens barrel 26 is driven to the rearmost end position by the second actuator 40 in the same manner as the second observation position, and assumes a state where a stopped state to which the second movable lens barrel 23 is attracted by a magnetic force from the third magnet 35 is held.

With such an operation, the image pickup apparatus 1 assumes the third observation position where the first movable lens barrel 23 and the second movable lens barrel 26 are moved to the rearmost end positions respectively.

Next, as shown in FIG. 6, the description is made with respect to a fourth observation position which is a fourth focus position where the first movable lens barrel 23 is moved to the rearmost end position, and the second movable lens barrel 26 is moved to an intermediate position within a movable range in the longitudinal direction.

The first movable lens barrel 23 is driven to the rearmost end position by the first actuator 30 in the same manner as the third observation position and, thereafter, the first movable lens barrel 23 is held at a stopped state to which the first movable lens barrel 23 is attracted by a magnetic force from the second magnet 34 even when the supply of electricity to the first coil 31 is stopped.

By supplying electricity to the second coil 32 of the second actuator 40 in the above-mentioned predetermined direction, the second movable lens barrel 26 is driven toward the front end side along the photographing optical axis O due to a magnetic force received from a generated magnetic field.

At this stage of operation, the first movable lens barrel 23 is in a stopped state at the rearmost end position, and the distal end surface 26*a* of the second movable lens barrel 26 is brought into contact with the end surface 25*a* of the contact portion 25 of the first movable lens barrel 23 and the second movable lens barrel 26 is stopped.

With such an operation, the image pickup apparatus 1 assumes the fourth observation position where the first movable lens barrel 23 is moved to the rearmost end position, and the second movable lens barrel 26 is moved to the intermediate position.

Next, as shown in FIG. 7, the description is made with respect to a fifth observation position which is a fifth focus position where the first movable lens barrel 23 is moved to an intermediate position within a movable range in a longitudinal direction, and the second movable lens barrel 26 is moved to the frontmost end position.

In this stage of operation, the second movable lens barrel 26 is driven to the frontmost end position by the second actuator 40 in the same manner as the first observation position and, thereafter, the second movable lens barrel 26 is held at a stopped state to which the second movable lens barrel 26 is attracted by a magnetic force from the second magnet 34 even when the supply of electricity to the second coil 32 is stopped.

Then, by supplying electricity to the first coil 31 of the first actuator 30 in a direction opposite to the above-mentioned predetermined direction, the first movable lens barrel 23 is driven toward the rear end side along the photographing optical axis O due to a magnetic force received from a generated magnetic field.

At this stage of operation, the second movable lens barrel 26 is in a stopped state at the frontmost end position, and the end surface 25*a* of the contact portion 25 of the first movable lens barrel 23 is brought into contact with the distal end surface 26*a* of the second movable lens barrel 26 and the first movable lens barrel 23 is stopped.

With such an operation, the image pickup apparatus 1 assumes the fifth observation position where the first movable lens barrel 23 is moved to the intermediate position, and the second movable lens barrel 26 is moved to the frontmost end position.

With such an operation, the image pickup apparatus 1 can switch from the first to fifth observation positions which become five focusing positions corresponding to the positions to which the first movable lens barrel 23 and the second movable lens barrel 26 are respectively moved.

In such an operation, a relationship in magnitude between a force which acts on the proximal end side of the first movable lens barrel 23 due to a magnetic force which is received from a magnetic field generated by the first actuator 30 and a force which acts on the distal end side of the second movable lens barrel 26 due to a magnetic force received from a magnetic field which the second actuator 40 generates is described with respect to the fourth observation position or the fifth observation position.

As shown in a graph in FIG. 8, a relationship between forces which act on the first movable lens barrel 23 and the second movable lens barrel 26 due to magnetic forces received from magnetic fields of the first actuator 30 and the second actuator 40 when the first movable lens barrel 23 or the second movable lens barrel 26 are moved to the fourth observation position or the fifth observation position is set in the image pickup apparatus 1.

First, for example, a case is described where the first movable lens barrel 23 and the second movable lens barrel 26 are moved from the third observation position shown in FIG. 9 to the fourth observation position (P4 in FIG. 8) shown in FIG. 10.

An electric current which is supplied to the first coil 31 is controlled such that a force F1 which acts on the proximal end side of the first movable lens barrel 23 is generated due to a magnetic force received from a magnetic field which the first actuator 30 generates.

An electric current which is supplied to the second coil 32 is controlled such that a force F2 which acts on the distal end side of the second movable lens barrel 26 which is smaller than the force F1 which acts on the proximal end side of the first movable lens barrel 23 (F1>F2) is generated due to a magnetic force received from a magnetic field which the second actuator 40 generates.

Accordingly, the first movable lens barrel 23 is moved to the rearmost end, the distal end surface 26*a* of the second movable lens barrel 26 is brought into contact with the end surface 25*a* of the contact portion 25 of the first movable lens barrel 23, and the second movable lens barrel 26 is stopped at an intermediate position.

In this manner, as shown in FIG. 10, the image pickup apparatus 1 assumes the fourth observation position where the first movable lens barrel 23 is moved to the rearmost end position, and the second movable lens barrel 26 is moved to the intermediate position which is a position away from the rearmost end position toward a front end side by a predetermined distance ΔL1.

Next, for example, a case is described where the first movable lens barrel 23 and the second movable lens barrel 26 are moved from the first observation position shown in FIG. 11 to the fifth observation position (P5 in FIG. 8) shown in FIG. 12.

An electric current which is supplied to the first coil 31 is controlled such that a force F3 which acts on the proximal end side of the first movable lens barrel 23 is generated due to a magnetic force received from a magnetic field which the first actuator 30 generates.

An electric current which is supplied to the second coil 32 is controlled such that a force F4 which acts on the distal end side of the second movable lens barrel 26 which is larger than the force F3 which acts on the proximal end side of the first movable lens barrel 23 (F4>F3) is generated due to a magnetic force received from a magnetic field which the second actuator 40 generates.

Accordingly, the second movable lens barrel 26 is moved to the frontmost end, the end surface 25*a* of the contact portion 25 of the first movable lens barrel 23 is brought into contact with the distal end surface 26*a* of the second movable lens barrel 26, and the first movable lens barrel 23 is stopped at an intermediate position.

In this manner, the image pickup apparatus 1 assumes the fourth observation position where the second movable lens barrel 26 is moved to the frontmost end position, and the first movable lens barrel 23 is moved to the intermediate position which is a position away from the frontmost end position toward a rear end side by a predetermined distance ΔL2.

In this manner, in the image pickup apparatus 1, at the fourth observation position and the fifth observation position, intensities of electric currents (quantities of electric currents) supplied to the first actuator 30 and the second actuator 40 are controlled. In other words, the forces F1, F2, F3, and F4 which act on the first movable lens barrel 23 and the second movable lens barrel 26 which are moving bodies are inversely proportional to a square of a distance between the first movable lens barrel 23 or the second movable lens barrel 26 and the first magnet 33, the second magnet 34, or the third magnet 35 and hence, a force relationship shown in the graph in FIG. 8 is obtained.

In the image pickup apparatus 1, even in a state where the supply of an electric current to the first actuator 30 and the second actuator 40 is stopped, the fourth observation position and the fifth observation position are maintained only by magnetic forces of the first magnet 33, the second magnet 34, or the third magnet 35.

As has been described above, in the image pickup apparatus 1 mounted on the endoscope 101 according to this embodiment, focusing switching can be performed at a plurality, that is five, of observation positions in this embodiment, corresponding to a distance from a subject. Accordingly, lowering of observability and treatment property of the endoscope 101 on a site to be examined can be prevented.

Further, the image pickup apparatus 1 has the miniaturized configuration where switching of optical characteristics, switching of focus positions in this embodiment, which differ from each other at five observation positions, can be performed without providing sensors for detecting the positions of the first movable lens barrel 23 and the second movable lens barrel 26 which are moving bodies.

Accordingly, in the endoscope 101 where the miniaturized image pickup apparatus 1 is mounted on the distal end portion 110 of the insertion section 102, the increase of a diameter of the insertion section 102 can be prevented and hence, the diameter of the insertion section 102 can be further reduced.

As has been described above, the image pickup apparatus 1 is a miniaturized image pickup apparatus which can perform multifocus switching without providing sensors for detecting the positions of the first movable lens barrel 23 and the second movable lens barrel 26, and the endoscope 101 on which the image pickup apparatus 1 is mounted can adopt the insertion section 102 having a narrow diameter.

First Modification

Figure 13:
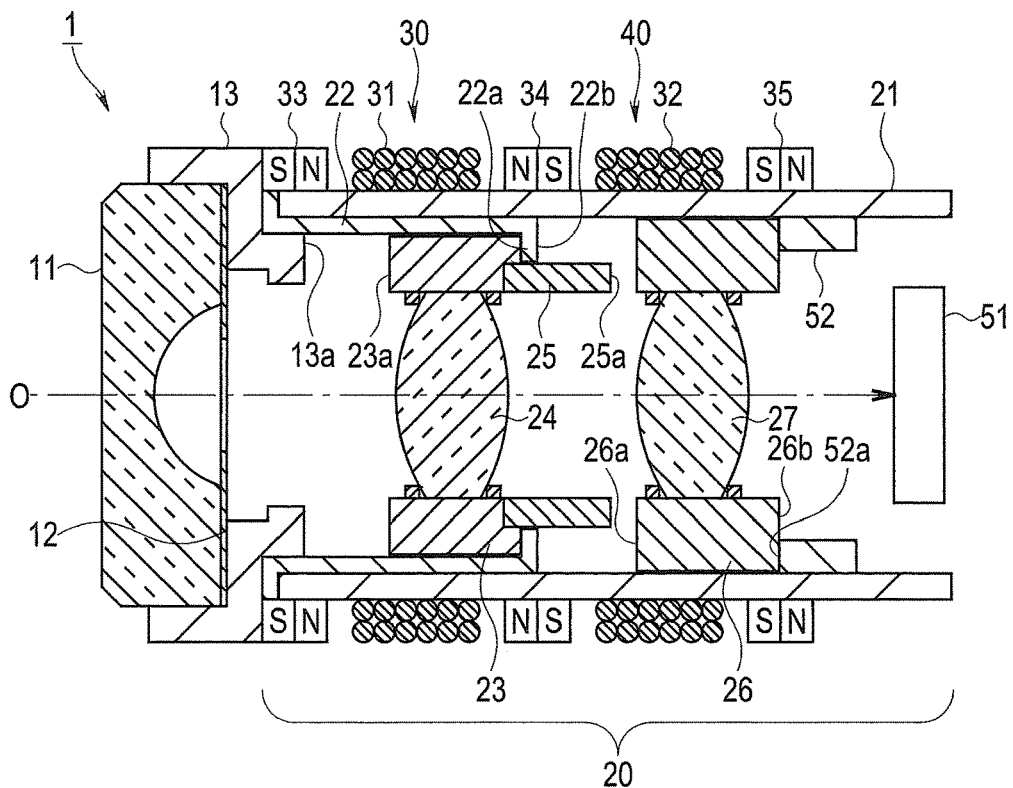
FIG. 13 is a cross-sectional view showing a configuration of an image pickup unit according to a first modification of one aspect of the present invention.

FIG. 13 is a cross-sectional view showing a configuration of an image pickup unit according to a first modification.

As shown in FIG. 13, an image pickup apparatus 1 may be configured such that a contact portion 25 is made of non-magnetic metal such as stainless steel, ceramic, or a rigid resin, and is fitted in a first movable lens barrel 23.

By forming the contact portion 25 by a non-magnetic member, the contact portion 25 is not affected by a magnetic force received from a magnetic field which a first actuator 30 generates, and the contact portion 25 does not interfere with the flow of a magnetic flux and hence, it is possible to suppress the contact portion 25 from affecting driving of the first movable lens barrel 23 in an advancing and retracting manner.

Second Modification

Figure 14:
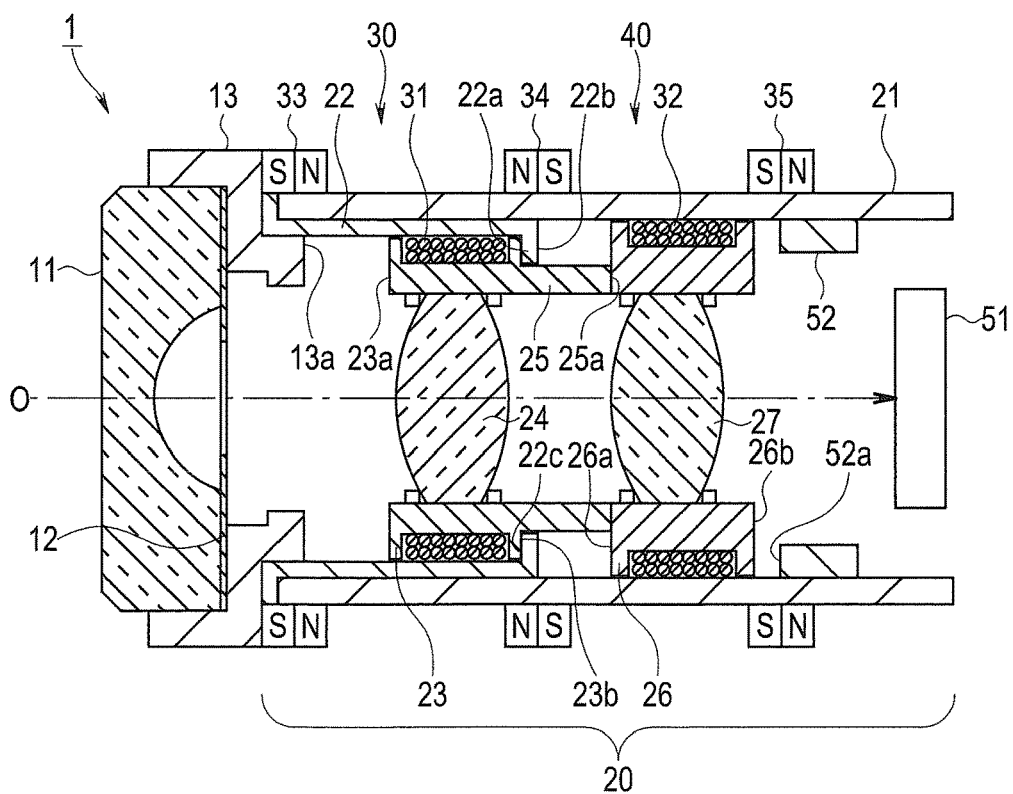
FIG. 14 is a cross-sectional view showing a configuration of an image pickup unit according to a second modification of one aspect of the present invention.

FIG. 14 is a cross-sectional view showing a configuration of an image pickup unit according to a second modification.

As shown in FIG. 14, an image pickup apparatus 1 may be configured such that a first coil 31 and a second coil 32 are disposed on a first movable lens barrel 23 side and a second movable lens barrel 26 side respectively.

Third Modification

Figure 15:
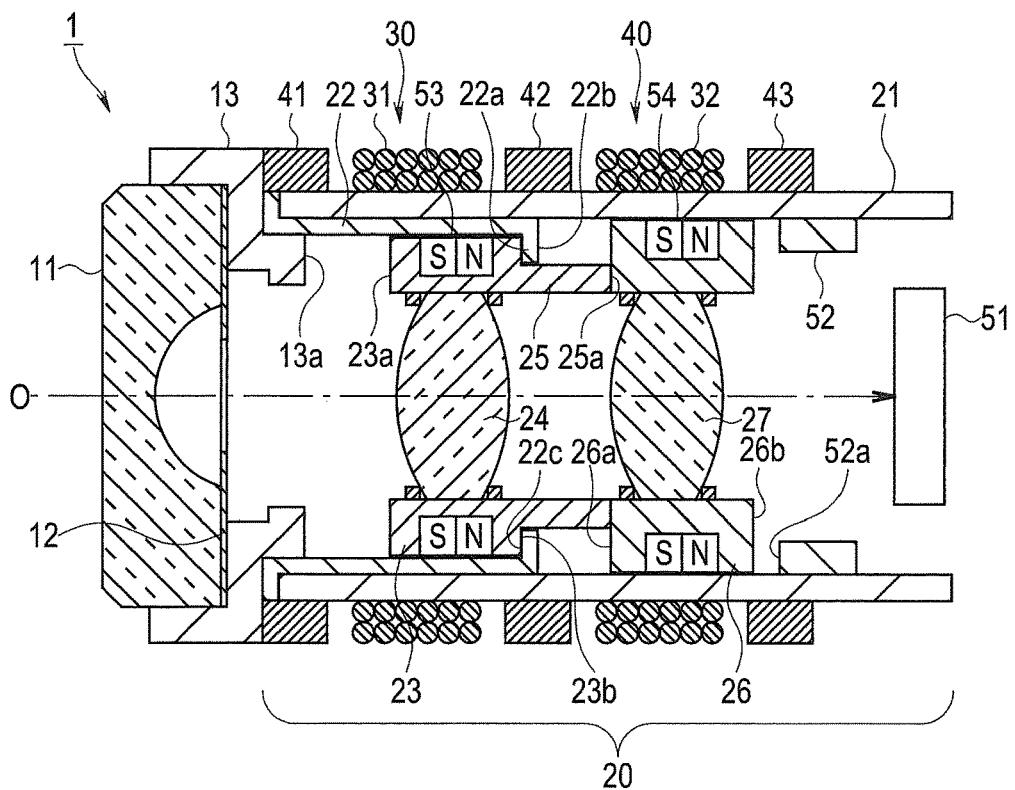
FIG. 15 is a cross-sectional view showing a configuration of an image pickup unit according to a third modification of one aspect of the present invention.

FIG. 15 is a cross-sectional view showing a configuration of an image pickup unit according to a third modification.

As shown in FIG. 15, an image pickup apparatus 1 may be configured such that the image pickup apparatus 1 includes magnets 53, 54 on a first movable lens barrel 23 side and a second movable lens barrel 26 side, and three yokes 41, 42, and 43 are provided in place of the first magnet 33, the second magnet 34, and the third magnet 35.

Fourth Modification

Figure 16:
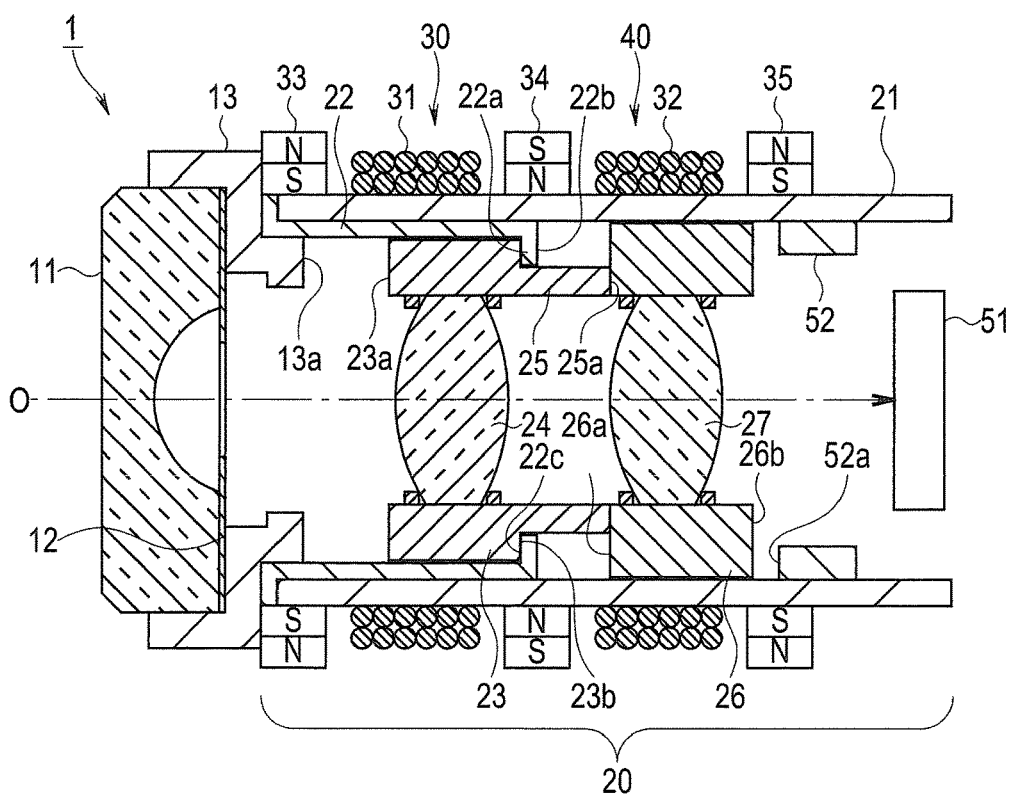
FIG. 16 is a cross-sectional view showing a configuration of an image pickup unit according to a fourth modification of one aspect of the present invention.

FIG. 16 is a cross-sectional view showing a configuration of an image pickup unit according to a fourth modification.

As shown in FIG. 16, an image pickup apparatus 1 may be configured such that a first magnet 33, a second magnet 34, and a third magnet 35 are magnetized in a radial direction such that polarities of these magnets 33, 34, and 35 have the same magnetization direction.

Fifth Modification

Figure 17:
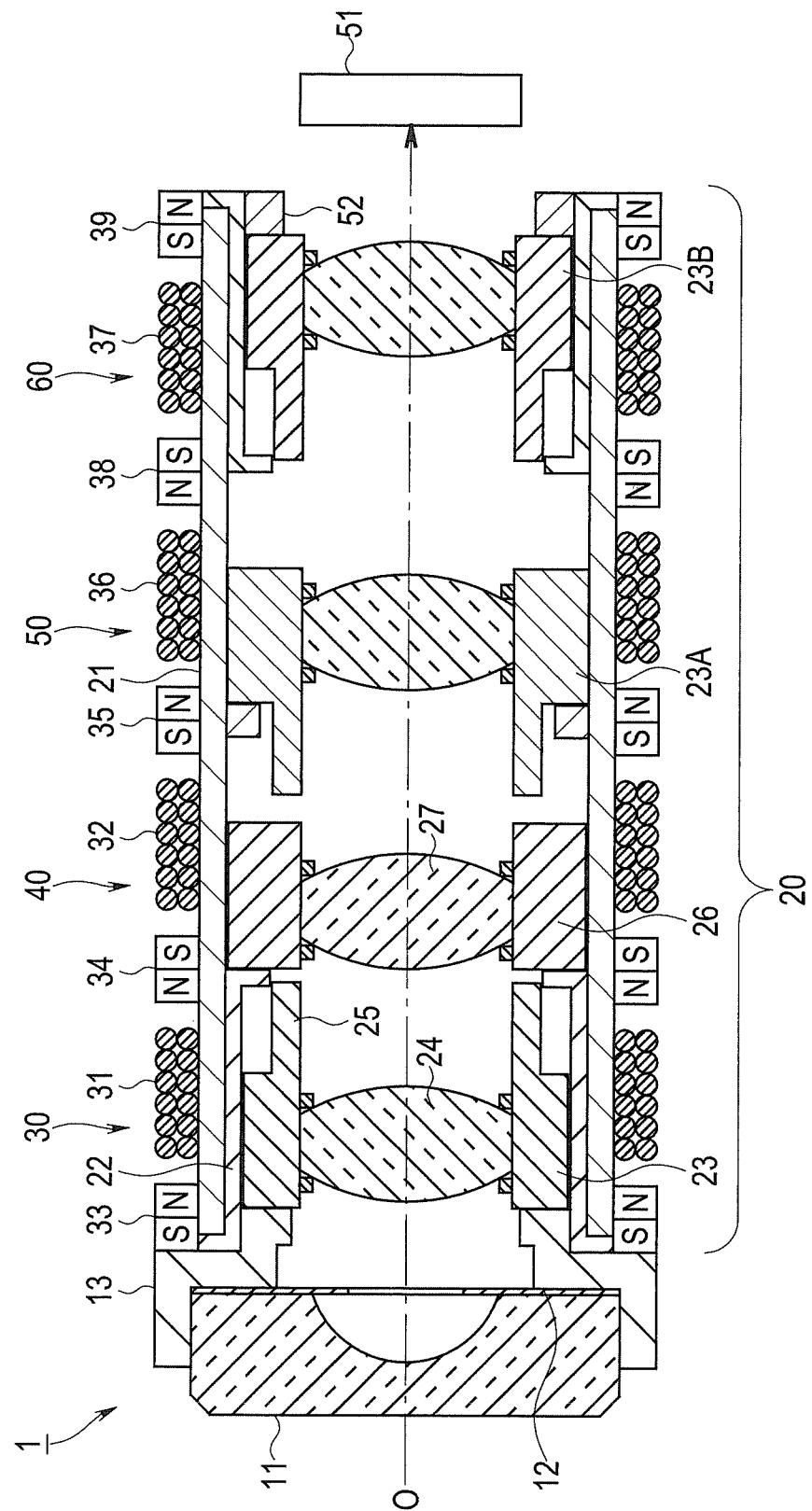
FIG. 17 is a cross-sectional view showing a configuration of an image pickup unit according to a fifth modification of one aspect of the present invention.

FIG. 17 is a cross-sectional view showing a configuration of an image pickup unit according to a fifth modification.

As shown in FIG. 17, an image pickup apparatus 1 may be configured such that the image pickup apparatus 1 includes, besides a first movable lens barrel 23 and a second movable lens barrel 26, a fourth movable lens barrel 23A which holds a third object optical system, a fifth movable lens barrel 23B which holds a fourth object optical system . . . , that is, a plurality of movable lens barrels which are three or more moving bodies. With such a configuration, the number of focus switching can be increased.

Sixth Modification

Figure 18:
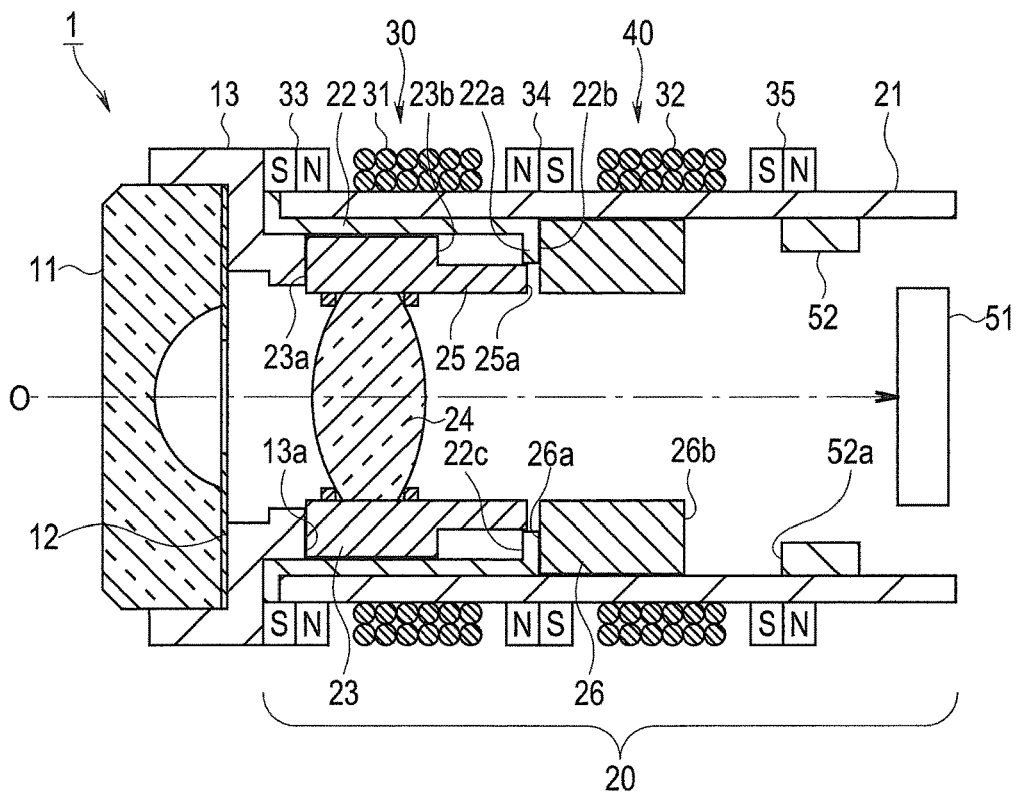
FIG. 18 is a cross-sectional view showing a configuration of an image pickup unit according to a sixth modification of one aspect of the present invention.

FIG. 18 is a cross-sectional view showing a configuration of an image pickup unit according to a sixth modification.

As shown in FIG. 18, the image pickup apparatus 1 may be configured such that only a first movable lens barrel 23 holds a movable lens (first movable lens) 24 which is an object optical system. In this modification, a second movable lens barrel 26 is merely a movable barrel which does not hold an object optical system.

Further, the image pickup unit according to the sixth modification may be configured such that the first movable lens barrel 23 is merely a movable barrel which does not hold an object optical system, and only the second movable lens barrel 26 holds a movable lens (second movable lens) 27 which is an object optical system.

Seventh Modification

Figure 19:
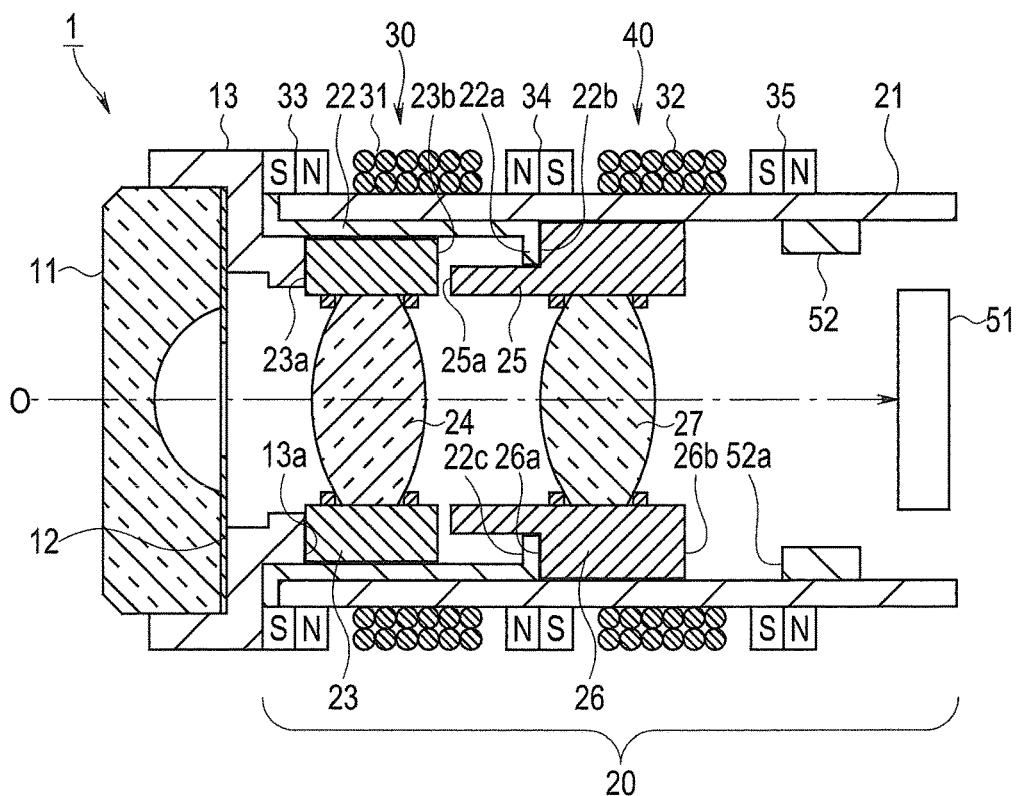
FIG. 19 is a cross-sectional view showing a configuration of an image pickup unit according to a seventh modification of one aspect of the present invention.

FIG. 19 is a cross-sectional view showing a configuration of an image pickup unit according to a seventh modification.

As shown in FIG. 19, an image pickup apparatus 1 may be configured such that a contact portion 25 may be mounted on a second movable lens barrel 26 instead of a first movable lens barrel 23.

An end surface 25*a* of a contact portion 25 forms a distal end side, and the movement of a first movable lens barrel 23 in a rear end direction or the movement of a second movable lens barrel 26 in a front end direction is restricted as the end surface 25*a* is brought into contact with a proximal end portion 23*b* of the first movable lens barrel 23.

The invention described in the above-mentioned embodiment is not limited to such an embodiment and the modifications of the embodiment, and various other modifications can be carried out without departing from the gist of the present invention in a stage where the present invention is carried out. Further, the above-mentioned embodiment includes the inventions at various stages, and various inventions can be extracted by suitably combining the plurality of components disclosed in the embodiment.

For example, even when some components are excluded from all components disclosed in the embodiment, the configuration formed after such exclusion of some components can be extracted as the invention provided that the previously-mentioned drawbacks can be overcome and the previously-mentioned advantageous effects can be acquired.

According to the present invention, it is possible to provide a miniaturized optical unit which can perform multifocus switching without providing a sensor which detects the position of the movable lens, and an endoscope on which the optical unit is mounted.

What is claimed is:

1. An optical unit comprising:
an image pickup optical system configured to form an image of an object image;
a first movable barrel configured to be advanceable and retractable in a direction of a photographing optical axis of the image pickup optical system;
a second movable barrel configured to be advanceable and retractable in the direction of the photographing optical axis independently from the first movable barrel;
an object optical system held by the first movable barrel and/or the second movable barrel, the object optical system forming a part of the image pickup optical system;
a first actuator configured to drive the first movable barrel in an advancing and retracting manner along the photographing optical axis;
a second actuator configured to drive the second movable barrel in an advancing and retracting manner along the photographing optical axis;
a first contact surface configured to define a first frontmost end position which the first movable barrel takes by being brought into contact with a distal end surface of the first movable barrel;
a second contact surface configured to define a first rearmost end position which the first movable barrel takes by being brought into contact with a proximal end surface of the first movable barrel;
a third contact surface configured to define a second frontmost end position which the second movable barrel takes by being brought into contact with a distal end surface of the second movable barrel;
a fourth contact surface configured to define a second rearmost end position which the second movable barrel takes by being brought into contact with a proximal end surface of the second movable barrel; and
a contact member formed on the first movable barrel, having a fifth contact surface configured to be brought into contact with the distal end surface of the second movable barrel in a state where the first movable barrel is moved to the first rearmost end position or in a state where the second movable barrel is moved to the second frontmost end position, the contact member being configured to define a first stop position which the first movable barrel takes between the first frontmost end position and the first rearmost end position or to define a second stop position which the second movable barrel takes between the second frontmost end position and the second rearmost end position.

2. The optical unit according to claim 1, wherein the first actuator and the second actuator are configured to switch an optical characteristic of the optical unit by driving the first movable barrel and the second movable barrel among:
a first observation position where the first movable barrel and the second movable barrel are moved to the first frontmost end position and the second frontmost end position respectively;
a second observation position where the first movable barrel is moved to the first frontmost end position and the second movable barrel is moved to the second rearmost end position;
a third observation position where the first movable barrel and the second movable barrel are moved to the first rearmost end position and the second rearmost end position respectively;
a fourth observation position where the first movable barrel is moved to the first rearmost end position and the second movable barrel is moved to the second stop position; and
a fifth observation position where the second movable barrel is moved to the second frontmost end position, and the first movable barrel is moved to the first stop position.

3. The optical unit according to claim 2, further comprising a fixed barrel in which the first movable barrel and the second movable barrel are disposed, wherein
the first actuator includes: a first magnet and a second magnet which are disposed on the fixed barrel in a spaced-apart manner from each other with a predetermined distance; and a first coil being wound around an outer peripheral portion of the fixed barrel between the first magnet and the second magnet, and
the second actuator includes: the second magnet used in common with the first actuator and a third magnet which are disposed on the fixed barrel in a spaced-apart manner from each other with a predetermined distance; and a second coil being wound around the outer peripheral portion of the fixed barrel between the second magnet and the third magnet.

4. The optical unit according to claim 3, wherein in a state where the first movable barrel and the second movable barrel are moved to the fourth observation position, a second quantity of an electric current which flows through the second coil of the second actuator is smaller than a first quantity of an electric current which flows through the first coil of the first actuator so that a second force which acts on the second movable barrel from the second actuator is smaller than a first force which acts on the first movable barrel.

5. The optical unit according to claim 2, further comprising a fixed barrel in which the first movable barrel and the second movable barrel are disposed, wherein
the first actuator includes: a first magnet and a second magnet which are disposed on the fixed barrel in a spaced-apart manner from each other with a predetermined distance; and a first coil being wound around an outer peripheral portion of the first movable barrel, and
the second actuator includes: the second magnet used in common with the first actuator and a third magnet which are disposed on the fixed barrel in a spaced-apart manner from each other with a predetermined distance; and a second coil being wound around an outer peripheral portion of the second movable barrel.

6. The optical unit according to claim 2, further comprising a fixed barrel in which the first movable barrel and the second movable barrel are disposed, wherein
the first actuator includes: a first magnet disposed on the first movable barrel; a first yoke and a second yoke disposed on the fixed barrel in a spaced-apart manner with a predetermined distance; and a first coil being wound around an outer peripheral portion of the fixed barrel between the first yoke and the second yoke, and the second actuator includes: a second magnet disposed on the second movable barrel; the second yoke used in common with the first actuator and a third yoke which are disposed on the fixed barrel in a spaced-apart manner from each other with a predetermined distance; and a second coil being wound around the outer peripheral portion of the fixed barrel between the second yoke and the third yoke.

7. The optical unit according to claim 3, wherein a quantity of an electric current which flows through the first coil and a quantity of an electric current which flows through the second coil are controlled, and the first movable barrel and the second movable barrel are driven to the fourth observation position or the fifth observation position in accordance with a relationship in magnitude between a first force generated by the first actuator for moving the first movable barrel toward a rear end side and a second force generated by the second actuator for moving the second movable barrel toward a front end side.

8. The optical unit according to claim 7, wherein the first movable barrel and the second movable barrel are maintained at the fourth observation position and the fifth observation position by a magnetic force of the first magnet, the second magnet or the third magnet in a state where supplying of an electric current to the first actuator and the second actuator is stopped.

9. An endoscope comprising:
an insertion section configured to be inserted into a subject; and
an optical unit mounted on a distal end portion of the insertion section, wherein
the optical unit includes:
an image pickup optical system configured to form an image of an object image;
a first movable barrel configured to be advanceable and retractable in a direction of an photographing optical axis of the image pickup optical system;
a second movable barrel configured to be advanceable and retractable in the direction of the photographing optical axis independently from the first movable barrel;
an object optical system held by the first movable barrel and/or the second movable barrel, the object optical system forming a part of the image pickup optical system;
a first actuator configured to drive the first movable barrel in an advancing and retracting manner along the photographing optical axis;
a second actuator configured to drive the second movable barrel in an advancing and retracting manner along the photographing optical axis;
a first contact surface configured to define a first frontmost end position which the first movable barrel takes by being brought into contact with a distal end surface of the first movable barrel;
a second contact surface configured to define a first rearmost end position which the first movable barrel takes by being brought into contact with a proximal end surface of the first movable barrel;
a third contact surface configured to define a second frontmost end position which the second movable barrel takes by being brought into contact with a distal end surface of the second movable barrel;
a fourth contact surface configured to define a second rearmost end position which the second movable barrel takes by being brought into contact with a proximal end surface of the second movable barrel; and
a contact member formed on the first movable barrel, having a fifth contact surface configured to be brought into contact with the distal end surface of the second movable barrel in a state where the first movable barrel is moved to the first rearmost end position or in a state where the second movable barrel is moved to the second frontmost end position, the contact member being configured to define a first stop position which the first movable barrel takes between the first frontmost end position and the first rearmost end position or to define a second stop position which the second movable barrel takes between the second frontmost end position and the second rearmost end position.

10. An optical unit comprising:
an image pickup optical system configured to form an image of an object image;
a first movable barrel configured to be advanceable and retractable in a direction of a photographing optical axis of the image pickup optical system;
a second movable barrel configured to be advanceable and retractable in the direction of the photographing optical axis independently from the first movable barrel;
an object optical system held by the first movable barrel and/or the second movable barrel, the object optical system forming a part of the image pickup optical system;
a first actuator configured to drive the first movable barrel in an advancing and retracting manner along the photographing optical axis;
a second actuator configured to drive the second movable barrel in an advancing and retracting manner along the photographing optical axis;
a first contact surface configured to define a first frontmost end position which the first movable barrel takes by being brought into contact with a distal end surface of the first movable barrel;
a second contact surface configured to define a first rearmost end position which the first movable barrel takes by being brought into contact with a proximal end surface of the first movable barrel;
a third contact surface configured to define a second frontmost end position which the second movable barrel takes by being brought into contact with a distal end surface of the second movable barrel;
a fourth contact surface configured to define a second rearmost end position which the second movable barrel takes by being brought into contact with a proximal end surface of the second movable barrel; and
a contact member formed on the second movable barrel, having a fifth contact surface configured to be brought into contact with the proximal end surface of the first movable barrel in a state where the first movable barrel is moved to the first rearmost end position or in a state where the second movable barrel is moved to the second frontmost end position, the contact member being configured to define a first stop position which the first movable barrel takes between the first frontmost end position and the first rearmost end position or to define a second stop position which the second movable barrel takes between the second frontmost end position and the second rearmost end position.

* * * * *